(12) United States Patent
Nagaoka et al.

(10) Patent No.: US 6,627,621 B2
(45) Date of Patent: Sep. 30, 2003

(54) NEUTROPHIL FUNCTION INHIBITORS

(75) Inventors: Isao Nagaoka, Yokohama (JP); Koji Sakamoto, Fujioka (JP)

(73) Assignee: Dainichieseika Color & Chemicals Mfg. Co., Ltd., Tokyo (JP)

( * ) Notice: Subject to any disclaimer, the term of this patent is extended or adjusted under 35 U.S.C. 154(b) by 146 days.

(21) Appl. No.: 09/906,771

(22) Filed: Jul. 18, 2001

(65) Prior Publication Data

US 2002/0128230 A1 Sep. 12, 2002

(30) Foreign Application Priority Data

Mar. 8, 2001 (JP) ........................................ 2001-064646

(51) Int. Cl.$^7$ ........................... A61K 31/70; C08B 37/00
(52) U.S. Cl. ........................................... 514/62; 536/53
(58) Field of Search ............................... 536/53; 514/62

(56) References Cited

U.S. PATENT DOCUMENTS 6,476,005 B1 * 11/2002 Petito et al. .................. 514/62

* cited by examiner

Primary Examiner—Kathleen K. Fonda
(74) Attorney, Agent, or Firm—Oblon, Spivak, McClelland, Maier & Neustadt, P.C.

(57) ABSTRACT

Glucosamine salts are effective for the inhibition of neutrophil functions, and hence, are useful for the prevention and/or treatment of diseases, caused as a result of an excessive extracellular release of active oxygen and antibiotic proteins by neutrophils, such as respiratory disease syndrome and adult respiratory disease syndrome. Use of glucosamine salts can, therefore, provide neutrophil function inhibitors, preventives and/or remedies for diseases caused as a result of an excessive extracellular release of active oxygen and antibiotic proteins by neutrophils, and also methods for the prevention and/or treatment of such diseases.

20 Claims, 5 Drawing Sheets

Generation of Active Oxygen by Neutrophils under FMLP Stimulation $*P < 0.05$  $**P < 0.01$ Generation of Active Oxygen by Neutrophils through Ingestion of Opsonized Zymosan (OPZ)

*$P < 0.05$

Ingestion of Opsonized Zymosan (OPZ) by Neutrophils

***P < 0.001

**P < 0.001

NEUTROPHIL FUNCTION INHIBITORS

BACKGROUND OF THE INVENTION

1) Field of the Invention

This invention relates to inhibitors of neutrophil functions (hereinafter called "neutrophil function inhibitors"), each of which comprises a glucosamine salt as an active ingredient. These neutrophil function inhibitors are useful as drugs, drinks, foods or the like for the prevention or treatment of troubles caused by exaltation of neutrophil functions, for example, respiratory disease syndrome (RDS), adult respiratory disease syndrome (ARDS) and other neutrophil-associated inflammations.

2) Description of the Related Art

A neutrophil is principal one of granules in a leukocyte. When an exogenous substance such as bacteria invades a living body, neutrophils emigrate to the invaded site, ingest the exogenous substance, have active oxygen generated and at the same time, antibiotic proteins (granules) such as lysozyme and defensins released, and play an important role to expel the exogenous substance under the action of the antibiotic proteins and also under the action of various acid hydrolases. However, an excessive extracellular release of these active oxygen and antibiotic proteins causes destruction of a tissue, and in some instances, further aggravates an acute inflammation occurred by the invasion of the exogenous substance. In the case of certain specific diseases such as respiratory distress syndrome, adult respiratory distress syndrome and other neutrophil-associated inflammations, this action of neutrophils is known to give adverse effects on these diseases.

Glucosamine salts, especially the sulfate or the hydrochloride have been produced, for example, by the process disclosed in JP1-28757 B or U.S. Pat. No. 3,683,076. U.S. Pat. No. 3,683,076 also discloses that glucosamine salts in the form of capsules or tablets are used as arthritis remedies and the like. However, absolutely nothing is known about effects of glucosamine salts on leukocytes.

SUMMARY OF THE INVENTION

Upon invasion of an exogenous substance into a living body, neutrophils play an important role to protect the living body from the exogenous substance. As has been described above, however, functions of neutrophils may give negative effects on the living body in some instances. An object of the present invention is to provide a drug or composition for preventing or lessening a trouble which may occur by such negative effects.

The present inventors have proceeded with a variety of research on effects of glucosamine salts which are hydrolyzates of chitosan and are substantially free of toxicity. As a result, it has been unexpectedly found that glucosamine salts have effects to inhibit functions of a neutrophil, one of the principal components of a leukocyte, for example, emigrating ability, ingesting action on exogenous substances, granule releasing ability, active oxygen releasing ability and the like, leading to the completion of the present invention.

In one aspect of the present invention, there is thus provided a neutrophil function inhibitor comprising a glucosamine salt as an active ingredient.

In another aspect of the present invention, there is also provided a preventive or remedy for a disease caused as a result of an excessive extracellular release of active oxygen and antibiotic proteins by neutrophils, comprising a glucosamine salt as an active ingredient.

In a further aspect of the present invention, there is also provided a dietetic drink or food for a disease caused as a result of an excessive extracellular release of active oxygen and antibiotic proteins by neutrophils, comprising a glucosamine salt as an active ingredient.

Specifically, the disease may be respiratory disease syndrome or adult respiratory disease syndrome.

In a still further aspect of the present invention, there is also provided a method for the prevention or treatment of respiratory disease syndrome or adult respiratory disease syndrome, which comprises administering an effective amount of a glucosamine salt to a human being.

In a still further aspect of the present invention, there is also provided use of a glucosamine salt for the prevention or treatment of respiratory disease syndrome or adult respiratory disease syndrome.

Specifically, the glucosamine salt may be selected from the group consisting of glucosamine sulfate, glucosamine hydrochloride, glucosamine acetate, glucosamine citrate and glucosamine malate.

Glucosamine salts can significantly inhibit the emigrating ability and ingesting action of neutrophils, the release of granules from neutrophils, and the release of active oxygen by neutrophils. Therefore, these glucosamine salts are useful as neutrophil function inhibitors, and can be employed as drugs, drinks, foods or the like for the prevention and/or treatment of troubles caused by exaltation of neutrophil functions, for example, respiratory disease syndrome, adult respiratory disease syndrome and other neutrophil-associated inflammations.

DETAILED DESCRIPTION OF THE INVENTION AND PREFERRED EMBODIMENTS

Figure 1:
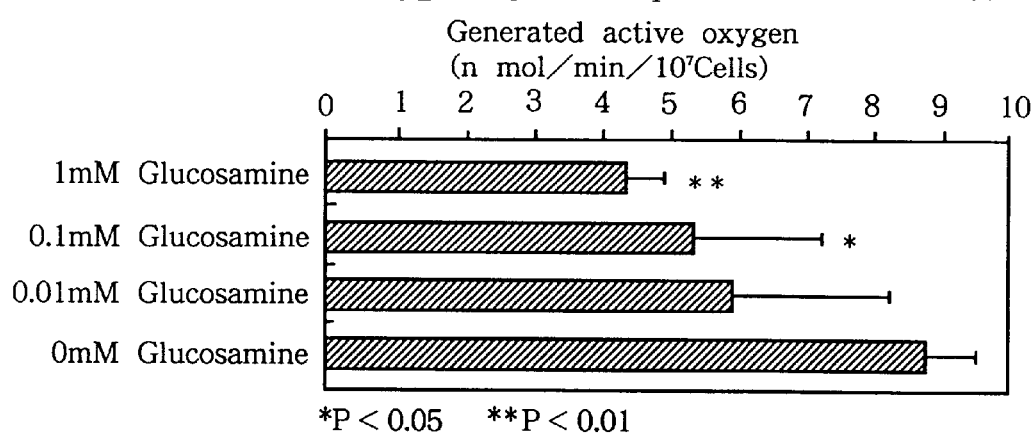
FIG. 1 is a bar graph showing variations in the amount of active oxygen generated by neutrophils under stimulation by FMLP as a function of the concentration of an added glucosamine salt.

No particular limitation is imposed on the glucosamine salt for use in the present invention insofar as it is pharmacologically acceptable. Inorganic acid salts and organic acid salts are both usable. In general, however, inorganic acid salts such as the sulfate and the hydrochloride are employed, with the hydrochloride being preferred in the present invention. Examples of organic acid salts usable in the present invention can include the acetate, the citrate and the malate.

The neutrophil function inhibitor according to the present invention may consist of the glucosamine salt alone, but generally, can be provided by formulating a glucosamine salt with drug, drink or food additives such as a carrier, an excipient and auxiliaries (a corrigent, a sweetener, a binder, etc.) into a liquid or solid preparation such as a tablet, a granule, a powder, a capsule or a jelly or into a composition such as a health promoting drink or food by a method known per se in the art. Examples of the carrier and excipient can include water and saccharides. The content of the glucosamine salt in the inhibitor may be, but is not limited to, generally 0.2% (by weight; this will hereinafter apply equally) or more, preferably 1% or more, and may range up to 100%.

Therefore, the term "neutrophil function inhibitor" as used herein can include glucosamine salts themselves, preparations obtained by mixing and formulating the glucosamine salts with excipients or the like, and those obtained by mixing the glucosamine salts with drinks or foods.

When a glucosamine salt is taken as a neutrophil function inhibitor according to the present invention by adding it to a drink or food, the glucosamine salt is mixed with an adequate drink or food. No particular limitation is imposed on the drink or food with which the glucosamine salt can be mixed. Illustrative of the drink or food are milk drinks such as milk, beverages such as health promoting drinks, and foods such as ham and sausages.

The content of the glucosamine salt in such a dietetic drink or food is not limited specifically, and may be generally 0.1% or more, preferably 0.3% or more, more preferably 0.5% or more, all based on the amount of the whole drink or food. No particular limitation is imposed on the upper limit of the content, but from the standpoint of taste and the like, the upper limit may be generally 10%, preferably 5%, more preferably 4%.

The daily dose per adult of the glucosamine salt as the neutrophil function inhibitor according to the present invention may be, but is not limited to, generally 0.3 g or more, preferably 0.5 g or more, more preferably 1 g or more. No particular limitation is imposed on the upper limit as the glucosamine salt is practically free of toxicity, but the upper limit may be generally 20 g, preferably 10 g, more preferably 5 g.

The neutrophil function inhibitor according to the present invention is useful as a preventive and/or a remedy for destruction of a tissue caused as a result of an excessive extracellular release of active oxygen and antibiotic proteins by neutrophils, for example, respiratory distress syndrome and adult respiratory distress syndrome. As neutrophils take part in the onset of an acute inflammation upon invasion of an exogenous substance such as bacteria, glucosamine salts are considered to be able to inhibit neutrophil-associated inflammations owing to their inhibitory effects on the functions of neutrophils. Accordingly, these glucosamine salts are also considered to be useful as inhibitors for inflammations of this type.

The present invention will hereinafter be described specifically based on the following Examples.

EXAMPLE 1

1. Preparation of Neutrophils Exuded into the Abdominal Cavity of a Guinea Pig

A glycogen solution (0.17% glycogen-0.9% NaCl solution) was administered into the abdominal cavity of a Guinea pig. About 15 hours later, the abdominal cavity was washed with a 0.4% sodium citrate-0.9% NaCl solution to collect an exudate. The exudate contained neutrophils of 95% or higher purity. After the abdominal cavity exudate was washed twice with phosphate buffer (pH 7.4), the neutrophils were suspended in phosphate buffer (pH 7.4) to prepare a neutrophil suspension.

2. Inhibition of Neutrophil Functions by a Glucosamine Salt

Inhibiting effects of a glucosamine salt on neutrophil functions were investigated with respect to the generation of active oxygen, ingesting effect and extra-cellular releasing effect on granular components by methods to be described subsequently herein. The results are shown in FIG. 1 through FIG. 4. Data are each shown as a mean ± standard deviation S.D. of three or more samples. Further, a test was conducted using an AVOVA.

(1) Inhibitory Effect of a Glucosamine Salt on the Generation of Active Oxygen

Glucosamine hydrochloride was added at 0.01 mM, 0.1 mM and 1 mM to aliquots of a neutrophil suspension (neutrophil concentration: $10^6$ cells/mL), respectively, followed by incubation at 37° C. for 20 minutes. To each of the reaction mixtures, N-formyl-1-methionyl-1-leucyl-1-phenylalanine (FMLP; $10^{-7}$ M) or opsonized zymosan (OPZ; count ratio of OPZ to neutrophils: 1:6) was added as an emigrating factor to stimulate neutrophils for 30 minutes. Generated active oxygen was measured by the cytochrome c reduction method.

Figure 2:
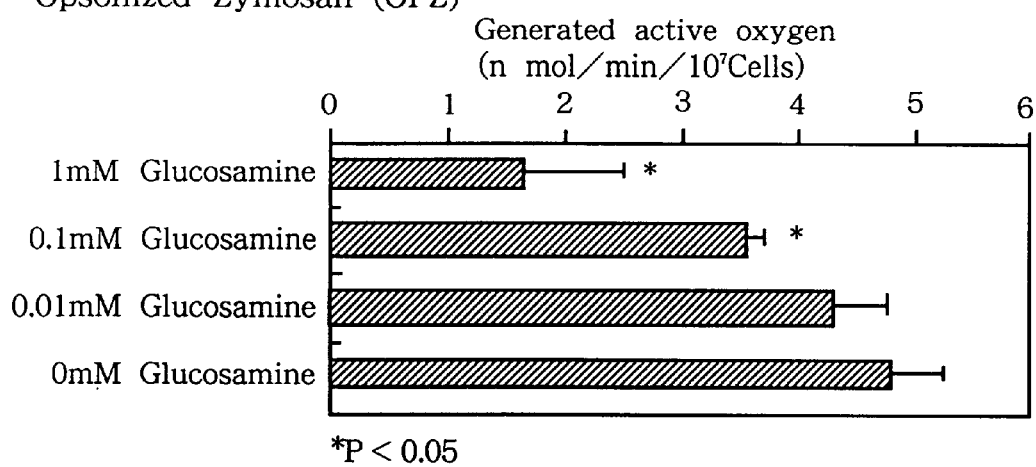
FIG. 2 is a bar graph showing variations in the amount of active oxygen generated by neutrophils through ingestion of opsonized zymosan (OPZ) as a function of the concentration of an added glucosamine salt.

The results obtained when FMLP was added are shown in FIG. 1, while the results obtained when OPZ was added are illustrated in FIG. 2.

Results: As is evident from FIG. 1 and FIG. 2, glucosamine hydrochloride inhibited in a concentration-dependent manner the formation of active oxygen by FMLP or opsonized zymosan.

Figure 3:
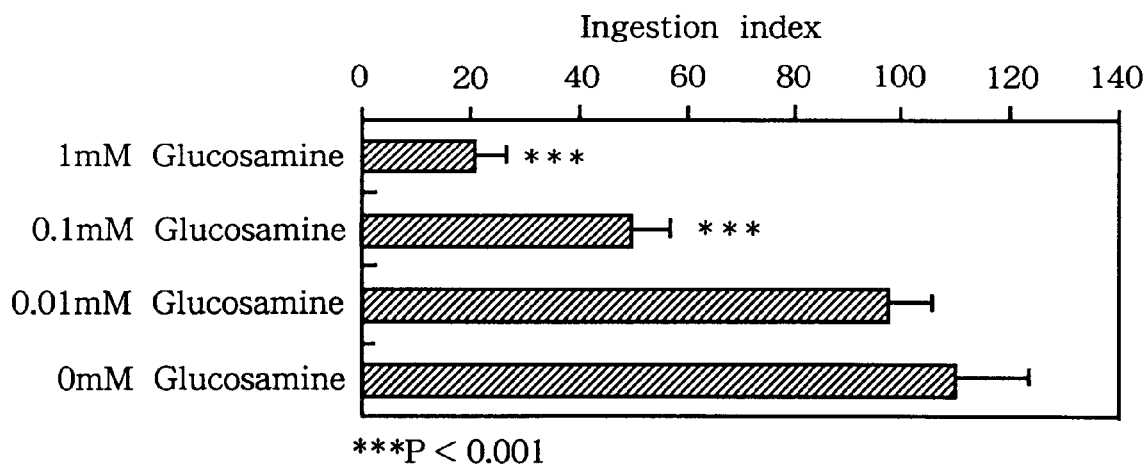
FIG. 3 is a bar graph showing, in terms of indexes, variations in the count of OPZ ingested by neutrophils as a function of the concentration of an added glucosamine salt.

(2) Inhibitory Effect of a Glucosamine Salt on the Ingesting Ability of Neutrophils Glucosamine hydrochloride was added at 0.01 mM, 0.1 mM and 1 mM to aliquots of a neutrophil suspension (neutrophil concentration: $10^7$ cells/mL), respectively, followed by incubation at 37° C. for 20 minutes. To each of the reaction mixtures, opsonized zymosan (OPZ; count ratio of OPZ to neutrophils: 1:6) was added, followed by a reaction for 30 minutes. The count of the yeast ingested by neutrophils was determined under a microscope, and was expressed in terms of an ingestion index. The results are shown in FIG. 3.

Results: The glucosamine salt inhibited in a concentration-dependent manner the ingestion of opsonized zymosan by neutrophils.

Figure 4:
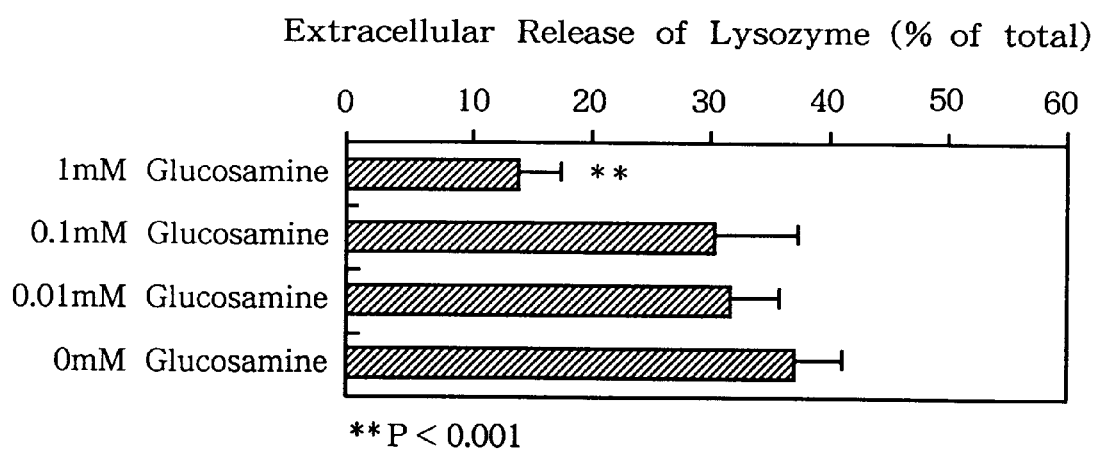
FIG. 4 is a bar graph showing variations in the activity of lysozyme released from neutrophils through ingestion of OPZ as a function of the concentration of an added glucosamine salt.

(3) Inhibitory Effect of a Glucosamine Salt on the Extracellular Release of Granular Components from Neutrophils Glucosamine hydrochloride was added at 0.01 mM, 0.1 mM and 1 mM to aliquots of a neutrophil suspension (neutrophil concentration: $10^7$ cells/mL), respectively, followed by incubation at 37° C. for 20 minutes. To each of the reaction mixtures, opsonized zymosan (OPZ; count ratio of OPZ to neutrophils: 1:6) was added, followed by a reaction for 30 minutes. The reaction mixture was centrifuged, the supernatant was collected, and then, the activity of the granular enzyme, lysozyme, released to the outside of cells was measured by calorimetrically quantitating dissolution of Micrococcus lysodeikticus cells. The results are shown in FIG. 4.

Results: As is readily appreciated from FIG. 4, the glucosamine salt significantly inhibited the extracellular release of the granular enzyme from neutrophils by opsonized zymosan.

(4) Inhibition of the Emigrating Ability of Neutrophils

Figure 5:
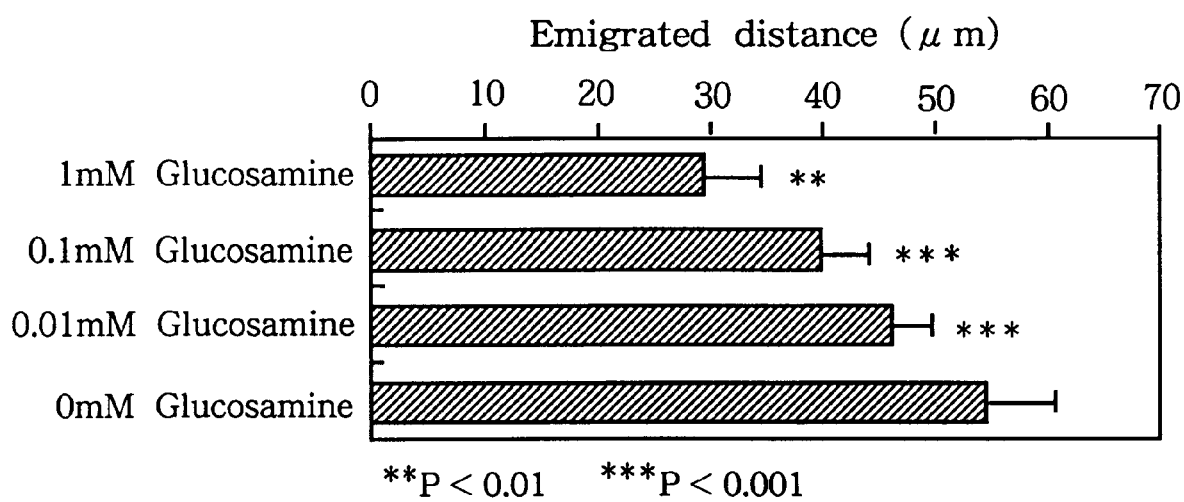
FIG. 5 is a bar graph showing variations in the emigrating ability of neutrophils as a function of the concentration of an added glucosamine salt.

The emigrating ability of neutrophils was measured by using as an emigrating factor the component factor C5 a generated by reacting fresh serum with a yeast. Described specifically, glucosamine hydrochloride was added at 0.01 mM, 0.1 mM and 1 mM to aliquots of a neutrophil suspension (neutrophil concentration: $3 \times 10^6$ cells/mL), respectively, followed by incubation at 37° C. for 20 minutes. The reaction mixtures were separately placed in Boyden's chambers each of which was equipped with a nitrocellulose membrane of 3 $\mu$m in pore size, and were then incubated at 37° C. for 20 minutes. After the reaction, distances over which neutrophils had emigrated were measured under a microscope. The results are shown in FIG. 5.

Results: As is readily envisaged from FIG. 4, the glucosamine salt inhibited in a concentration-dependent manner the emigrating ability of neutrophils.

What is claimed is:

1. A method for treating respiratory disease syndrome (RDS), adult respiratory disease syndrome (ARDS), or a disease associated with the extracellular release of active oxygen and antibiotic protein by neutrophils, comprising administering to a subject in need thereof an effective amount of at least one glucosamine salt.

2. The method of claim 1 comprising treating a subject who has RDS.

3. The method of claim 1 comprising treating a subject who has ARDS.

4. The method of claim 1 comprising treating a subject who has a disease associated with the extracellular release of active oxygen and antibiotic proteins by neutrophils.

5. The method of claim 1 comprising administering an effective amount of an inorganic acid glucosamine salt.

6. The method of claim 1 comprising administering an effective amount of an organic acid glucosamine salt.

7. The method of claim 1 comprising administering an effective amount of glucosamine sulfate.

8. The method of claim 1 comprising administering an effective amount of glucosamine hydrochloride.

9. The method of claim 1 comprising administering an effective amount of glucosamine acetate.

10. The method of claim 1 comprising administering an effective amount of glucosamine citrate.

11. The method of claim 1 comprising administering an effective amount of glucosamine malate.

12. The method of claim 1 comprising administering two or more glucosamine salts.

13. The method of claim 1 comprising administering said glucosamine salt in combination with one or more excipient(s), carrier(s) or auxiliary(ies).

14. The method of claim 1 comprising administering said glucosamine salt in combination with a food.

15. The method of claim 1 comprising administering said glucosamine salt in combination with a beverage.

16. The method of claim 1 comprising administering said glucosamine salt in combination with a beverage, wherein the content of said at least one glucosamine salt ranges from 0.1% to 10% by weight.

17. The method of claim 1 comprising administering said at least one glucosamine salt in combination with a beverage, wherein the content of said at least one glucosamine salt ranges from 0.5% to 4% by weight.

18. The method of claim 1 comprising administering said at least one glucosamine salt in combination with a milk product.

19. The method of claim 1 comprising administering said at least one glucosamine salt in combination with a meat product.

20. The method of claim 1 comprising administering said glucosamine salt in combination with a drug.

* * * * *